US00PP26727P2

(12) United States Plant Patent
Bergeron

(10) Patent No.: US PP26,727 P2
(45) Date of Patent: May 10, 2016

(54) ***HOSTA* PLANT NAMED 'ROYAL WEDDING'**

(50) Latin Name: ***Hosta* hybrid (Tratt.)**
Varietal Denomination: Royal Wedding

(71) Applicant: Amy J. Bergeron, Holland, MI (US)

(72) Inventor: Amy J. Bergeron, Holland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 153 days.

(21) Appl. No.: 13/999,412

(22) Filed: Feb. 24, 2014

(51) Int. Cl.
*A01H 5/12* (2006.01)

(52) U.S. Cl.
USPC ..... Plt./353

(58) Field of Classification Search
USPC ..... Plt./353
See application file for complete search history.

(56) References Cited

PUBLICATIONS

Perennial Resource *Hosta* Royal Weeding PPAF 2015 retrieved on Sep. 10, 2015, retrieved from the Internet at <http://www.perennialresource.com/encyclopedia/view/?plant=2383> pp. 1-3.*
Susan Martin, Walters Gardens, Inc. Wholesale Catalog, Summer 2013-Spring 2014, Jul. 2013, front cover and p. 140, Walters Gardens, Inc., Zeeland, Michigan, US.
Walters Gardens, Inc. first sales of *Hosta* 'Royal Wedding', computer printout from search, 3 pp. 2013-2014.

* cited by examiner

*Primary Examiner* — June Hwu

(57) ABSTRACT

A new and distinct *Hosta* plant named 'Royal Wedding' with foliage having blades of wide variegated creamy-white to near white margins, and dark center with minor intermediate feathering colors. The plant habit is compact and rounded in habit with sweetly fragrant white flowers just above foliage in mid to late summer.

2 Drawing Sheets

LATIN NAME AND VARIETY DENOMINATION OF THE PLANT

Botanical classification: *Hosta* hybrid (Tratt.).
Variety denomination: 'Royal Wedding'.

CROSS REFERENCE TO RELATED PLANTS

There are over 5,000 registered *Hosta* cultivars with The American *Hosta* Society, which is the International Cultivar Registration Authority for the genus *Hosta* and a similar number of unregistered cultivars. Only one species and a small number of these cultivars have fragrant flowers, and a smaller number still have variegated foliage and white flowers. *Hosta* 'Royal Wedding' is a natural, un-induced, whole-plant mutation from 'Diana Remembered' (not patented). 'Diana Remembered' is a stable variegated form of the streaked and unstable cultivar *Hosta* 'Seventh Heaven' (not patented) which is a selection from a cross between *Hosta* 'Kevin Vaughn' (not patented)×*Hosta plantaginea*. Other fragrant, light-margined *hostas* include: 'Austin Dickinson' (not patented), 'Emily Dickinson' (not patented), 'Fragrant King' (not patented), 'Fragrant Queen' U.S. Plant Pat. No. 19,508, 'Iron Gate Glamour' (not patented), 'Iron Gate Special'; (not patented), 'Mistress Mabel' (not patented), 'So Sweet' (not patented), 'Summer Fragrance' (not patented) and 'White Margin' U.S. Plant Pat. No. 8,015. All of the above *Hosta* cultivars have fragrant flowers and variegated foliage with green centers and lighter margins.

FEDERALLY SPONSORED RESEARCH

This invention was developed without any federally sponsored research or development funding.

BACKGROUND AND ORIGIN OF THE PLANT

The present invention relates to a new and distinct *hosta* plant, *Hosta* 'Royal Wedding' hereinafter also referred to as the new plant or just the cultivar name, 'Royal Wedding'. *Hosta* 'Royal Wedding' was discovered by Amy J. Bergeron as a non-induced, naturally-occurring, whole-plant mutation in a batch of tissue cultured propagated *Hosta* 'Diana Remembered' (not patented) at a wholesale nursery greenhouse in Zeeland, Mich., USA on Mar. 29, 2010. The new plant has been asexually propagated by division at the same nursery in Zeeland, Mich. USA since 2012 and also by careful shoot tip plant tissue culture with the resultant asexually propagated plants having retained all the same traits as the original plant. 'Royal Wedding' is stable and reproduces true to type in successive generations of asexual reproduction.

BRIEF SUMMARY OF THE PLANT

The nearest comparison variety is *Hosta* 'Diana Remembered', and the new plant, 'Royal Wedding', differs by having wider variegated margins, thicker substance to the foliage and slightly darker green leaf centers.

Distinctions between the above listed comparison cultivars and the new plant are further delineated in Table 1 below.

TABLE 1

Cultivar Comparisons

| CULTIVAR | MARGIN COLOR | MARGIN WIDTH | LEAF SHAPE | FLOWER COLOR |
|---|---|---|---|---|
| 'Austin Dickinson' | creamy white | medium | ovate | purple |
| 'Diana Remembered' | creamy white | medium | rounded | white |
| 'Emily Dickinson' | creamy white | thin | ovate | light purple |
| 'Fragrant King' | creamy yellow | wide | rounded | pale lavender |
| 'Fragrant Queen' | creamy white | wide | rounded | pale lavender |
| 'Iron Gate Glamour' | creamy white | medium | ovate | purple |
| 'Iron Gate Special' | near white | medium | ovate | pale lavender |
| 'Mistress Mabel' | creamy white | medium | ovate | light lavender |
| 'Royal Wedding' | creamy white | wide | rounded | white |
| 'So Sweet | creamy white | narrow | ovate | lavender |
| 'Summer Fragrance' | creamy yellow | medium | ovate | lavender |

Other *Hosta* cultivars have short habit and variegation of a similar nature, or other individual traits similar to 'Royal Wedding' but the new plant differs from the above cultivars and all other *hostas* known to the applicant, by the combination of the following traits:

1. Compact rounded plant habit;
2. Variegated foliage with wide creamy-white to near-white margins, green center and minor intermediate feathered colors between;
3. White fragrant flowers just above foliage; and
4. Stiff scapes and leaves with thick substance.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

The first drawing shows a three-year old *Hosta* 'Royal Wedding' plant in a container in mid-season grown in a shaded greenhouse at a nursery in Zeeland, Mich. with supplement fertilizer and water as needed.

FIG. 2 shows a close-up of the scape and flowers of *Hosta* 'Royal Wedding'.

DETAILED BOTANICAL DESCRIPTION

The following descriptions and color references are based on the 2001 edition of The Royal Horticultural Society Colour Chart except where common dictionary terms are used. The new plant, *Hosta* 'Royal Wedding', has not been observed under all possible environments. The phenotype may vary slightly with different environmental conditions, such as temperature, light, fertility, moisture and maturity levels, but without any change in the genotype. The following observations and size descriptions are of a potted three-year old plant in a shaded greenhouse in Zeeland, Mich. with supplemental water and fertilizer.

Botanical classification: *Hosta*×hybrid.

Parentage: Whole-plant mutation of *Hosta* 'Diana Remembered' (not patented).

Propagation: Garden division and sterile plant tissue culture.

Time to initiate roots from tissue culture: About two to three weeks.

Growth rate: Rapid.

Crop time: About 10 to 12 weeks to finish during the summer in a one-liter container from rooted tissue culture plantlet.

Rooting habit: Normal, fleshy, lightly branching.

Plant shape and habit: Hardy herbaceous perennial with basal rosette of leaves emerging from rhizomes producing a short symmetrical mound of broadly horizontal leaves.

Plant size: Foliage height 30.0 to 34.0 cm above soil line to the top of the leaves and 50.0 to 56.0 cm wide at the widest point slightly above the soil line.

Foliage description: Entire, glabrous, slightly glaucous above and becoming lustrous my mid-season, lustrous below; cordate, broadly acute leaf apex with cordate base; slightly sinuate; medium blistering or dimpling, up to about 4.0 mm deep in between veins; twisting absent; margin undulation weak.

Leaf blade: Cordate, becoming more rounded with maturity; about 13.0 cm long and 10.0 cm wide; dark green center and light yellow margin that varies in width from 16 mm to 36 mm wide at broadest portion of leaf blade.

Leaf blade color: Early season shortly after emergence adaxial (top) center color between RHS 135A and RHS 135B; early season adaxial margin nearest RHS 150D; early season abaxial (underside) center nearest RHS 135B; early season abaxial margin between RHS 150D and RHS 145D; other intermediate colors in irregular patches and stripes between the margin and center portions normally jutting toward the leaf blade center on both adaxial and abaxial sides comprising nearest RHS 138D, RHS N144C, RHS 142D and RHS 144D; mid-season and later summer adaxial centers between RHS 135B and RHS N 134A; mid-season and later adaxial margins near white, lighter than RHS 155D; mid-season and later abaxial center between RHS 139B and RHS 136C; mid-season and later abaxial margins near white, lighter than RHS 155D; intermediate colors where adaxial and abaxial leaf blade margins and centers unevenly and irregularly fold over each other comprising: larger portions of nearest RHS 138D, and smaller portions of nearest RHS 157B, nearest RHS 144D, lighter than RHS N144D, and nearest RHS 145C.

*Petiole*.—Entire, glabrous, concavo-convex; mostly straight from base of plant to leaf base with little bending or curving, stiff; between 8.0 to 12.0 cm long and 10.0 to 13.0 mm wide at base, average about 10 cm long and 12 mm wide.

*Petiole color*.—Adaxial and abaxial centers between RHS 137B and RHS 136B; adaxial and abaxial margins nearest RHS 157C.

*Veins*.—Parallel, raised on abaxial side, normally 9 pairs and one main center vein.

*Veins color*.—Adaxial and abaxial veins the same color as the surrounding tissue.

Flower description:

*Buds one day prior to opening*.—Globose with rounded apex and narrow base; about 1.5 cm in diameter with base narrowing at about mid-length to about 0.4 cm diameter; about 4.5 cm long.

*Bud color*.—White, lighter than RHS 155D.

*Flowers*.—Perfect; funnelform; held nearly horizontal with pedicel at 90 degree angle to peduncle; about 7.0 cm wide and 6.0 cm long, fused portion about 2.5 cm long and 3.0 mm diameter (distal flowers smaller); persists for a normal period, usually one day on plant or as cut flower; scapes remain effective with flowers from mid-August to mid-September with 16 to 22 flowers per scape; attitude nearly horizontal to slightly drooping.

*Fragrance*.—Pleasant, lightly sweet.

*Tepal*.—Two nearly identical sets of three, glabrous, entire; fused at base; with acute apex; inner set approximately 7.5 cm long and 2.0 cm wide; outer set approximately 7.5 cm long and 2.2 cm wide.

*Tepal color*.—Coloring of both sets identical; adaxial and abaxial centers and margins white, lighter than RHS 155D.

*Tepal veins*.—Three nearly indistinguishable in center of tepal.

*Tepal vein color*.—White, lighter than RHS 155D.

*Gynoecium*.—Single; tri-carpelled. Style: single, approximately 7.5 cm long, 1.5 mm diameter, curved upward in distal 1.0 cm about 90 degrees; color lighter than RHS 155D. Stigma: globose, about 2 mm in diameter; color lighter than RHS 155D. Ovary; ovoid, about 7.0 mm long and 3.0 mm diameter at widest; color nearest RHS 145B.

*Androecium*.—Filaments: six, approximately 7.0 cm long and 1.0 mm in diameter; curved upward to nearly 90 degrees in the apical 1.0 cm; color lighter than RHS 155D. Anthers: elliptic; dorsifixed, longitudinally dehiscent; about 4.0 mm long and 1.5 mm wide; color between RHS N187A and RHS N186B along perimeter and nearest RHS N170D in the center where attached to filament. Pollen: elliptic, less than 0.1mm long, color between RHS 14C and RHS 11A.

*Peduncle*.—Usually one per mature division; glaucous, glabrous; nearly slightly angled to 30 degrees from vertical with slight curve at distal end; 45 to 50 cm tall, and up to 8.0 mm in diameter at base.

*Peduncle color*.—Nearest RHS 139A in the lower portion and nearest RHS 139B in the upper portion.

*Pedicel*.—Short, glabrous; approximately 8.0 mm long and 2.5 mm diameter; nearest RHS 139B.

*Scape bracts*.—Each flower normally subtended by a single bract with sometimes one or rarely two below the first flower; size varies with immature plants usually resembling leaves in size and shape; average fit bract average 10 cm long and 5 cm wide, acute apex, sessile base partially clasping, concaved supporting flower, decreasing in size distally; bracts subtending flowers protruding to nearly perpendicular to scape.

*Scape bract color*.—At time of flowering adaxial center between RHS 137C and RHS 137B, adaxial and abaxial margin lighter than RHS 155D and more green than RHS 11C; abaxial centers between RHS 137B and RHS 137C.

Fruit: Tri-valved dehiscent capsule; elliptic, about 2.7 cm long and 5.0 mm diameter; color when mature nearest RHS 161C.

Seed: About 24 per capsule; endospermic; flattened-elliptic wing surrounding embryo situated toward one end of ellipse; about 7.0 mm long and 2.0 mm wide and 1.0 mm thick at embryo; color nearest RHS 202A.

Disease tolerance and resistance: The new plant has not shown any resistance to pests and diseases common to *hostas*. *Hosta* 'Royal Wedding' is capable of tolerating more heat and sunlight than typical *hostas* and requires less vernalization to emerge and grow well. The plant grows best and shows best coloration with plenty of moisture, adequate drainage and light shade, but is able to tolerate some drought when mature, and tolerates direct sun without leaf burn, especially during the cooler parts of the day and when provided sufficient water. Hardiness at least from USDA zone 3 through 9, and other disease resistance is typical of that of other *hostas*.

I claim:

1. A new and distinct ornamental plant cultivar named *Hosta* 'Royal Wedding' as herein described and illustrated.

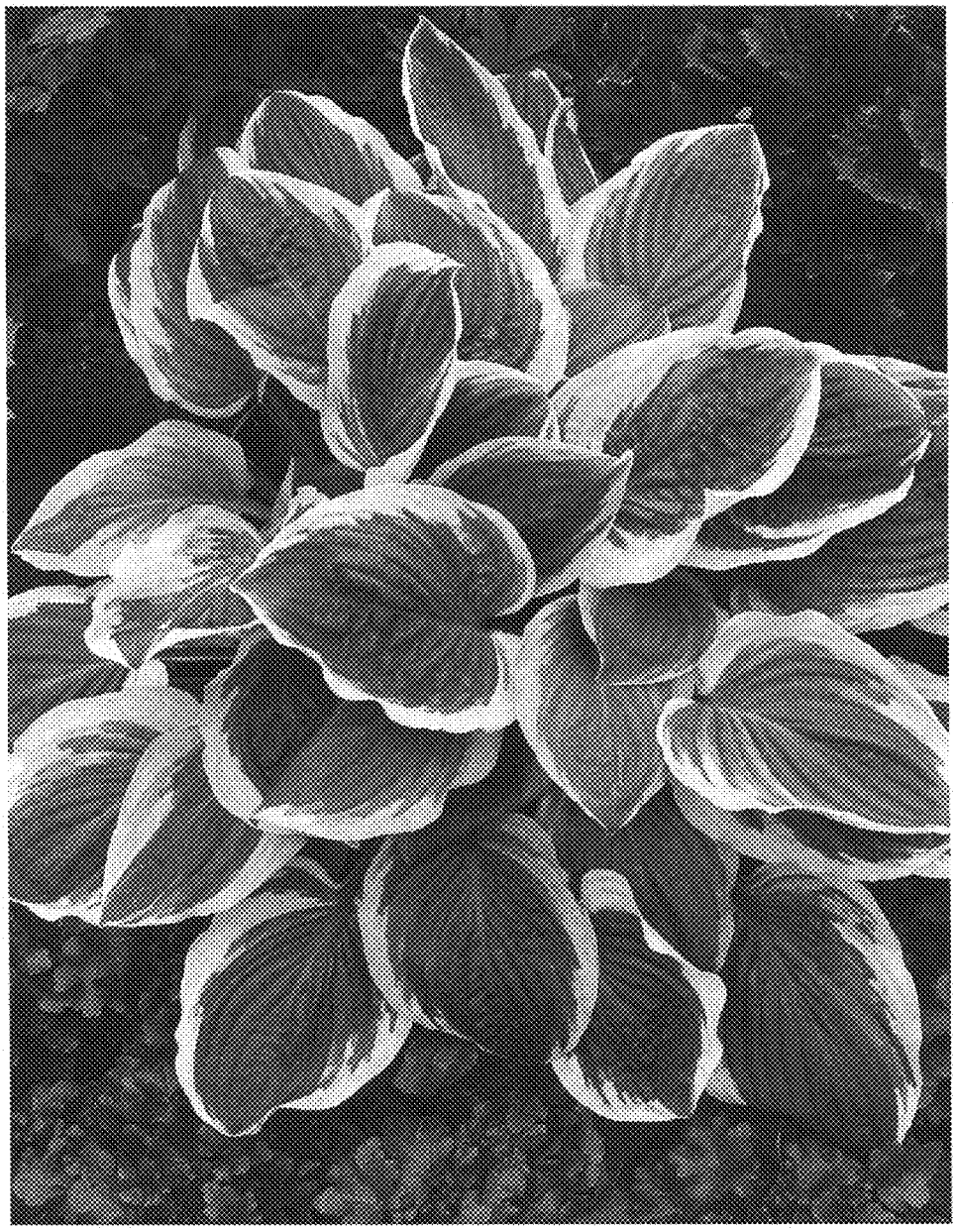

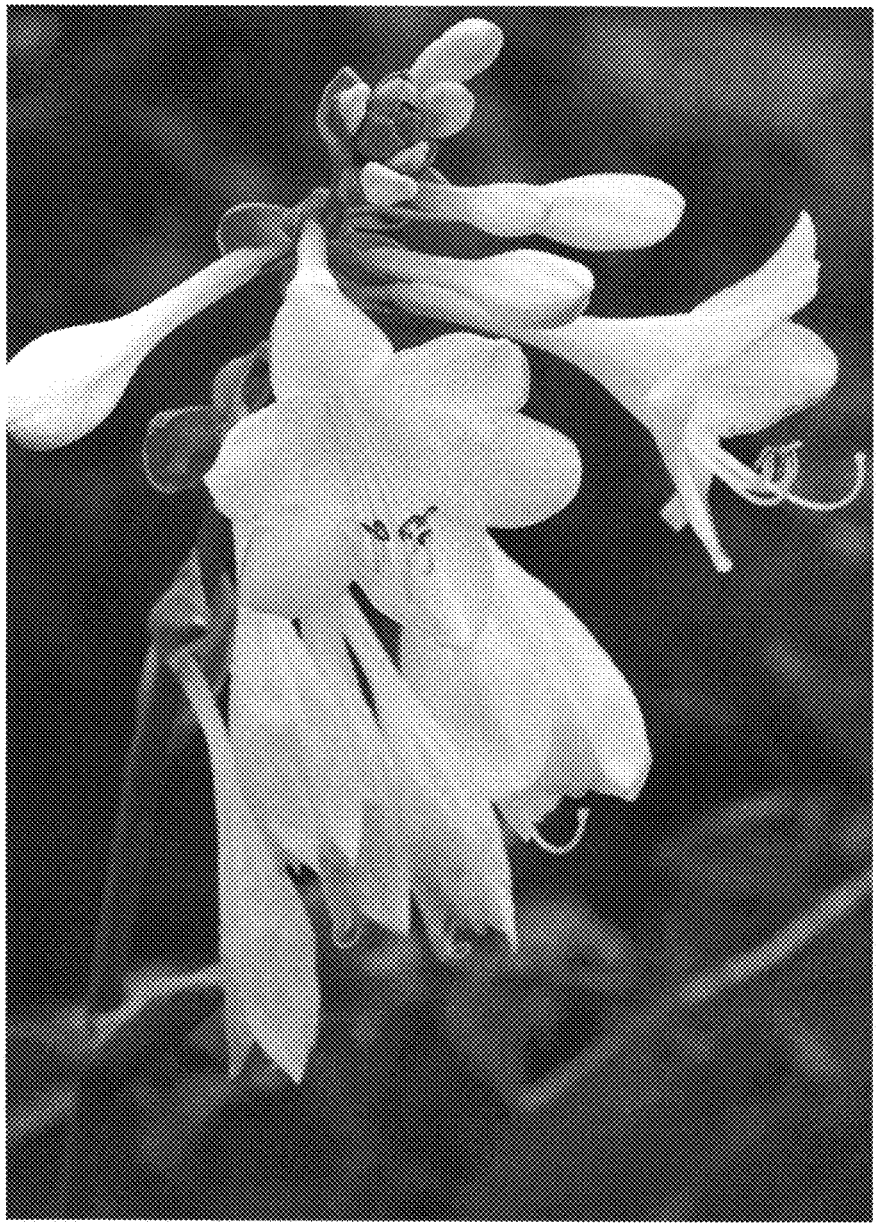

* * * * *